United States Patent
Mingozzi et al.

(10) Patent No.: US 9,289,239 B2
(45) Date of Patent: Mar. 22, 2016

(54) EXTERNAL FIXATION DEVICE

(75) Inventors: Franco Mingozzi, Calderara di Reno (IT); Alan Dovesi, Bologna (IT); Thomas Gausepohl, Marl (DE)

(73) Assignee: CITIEFFE S.r.l. (IT)

( * ) Notice: Subject to any disclaimer, the term of this patent is extended or adjusted under 35 U.S.C. 154(b) by 44 days.

(21) Appl. No.: 14/128,380

(22) PCT Filed: Jun. 12, 2012

(86) PCT No.: PCT/IB2012/052955
§ 371 (c)(1),
(2), (4) Date: Dec. 20, 2013

(87) PCT Pub. No.: WO2013/001393
PCT Pub. Date: Jan. 3, 2013

(65) Prior Publication Data
US 2014/0135766 A1    May 15, 2014

(30) Foreign Application Priority Data
Jun. 27, 2011   (IT) ............................... BO2011A0370

(51) Int. Cl.
*A61F 5/04*        (2006.01)
*A61B 17/64*       (2006.01)

(52) U.S. Cl.
CPC ......... *A61B 17/6458* (2013.01); *A61B 17/6425* (2013.01); *A61B 17/6433* (2013.01); *A61B 17/6475* (2013.01); *A61B 17/6483* (2013.01)

(58) Field of Classification Search
CPC ........ A61B 17/60; A61B 17/62; A61B 17/64; A61B 17/6416; A61B 17/6425; A61B 17/6441; A61B 17/645; A61B 17/6458; A61B 17/6466; A61B 17/6475; A61B 17/6483; A61B 17/6491; A61B 17/66; A61B 17/663; A61B 19/50; A61B 17/025; A61B 2017/0268; A61B 2019/508
See application file for complete search history.

(56) References Cited

U.S. PATENT DOCUMENTS

| | | | | |
|---|---|---|---|---|
| 2,250,417 | A * | 7/1941 | Ettinger | A61B 17/60 606/54 |
| 4,573,459 | A * | 3/1986 | Litton | A61B 17/66 606/58 |

(Continued)

FOREIGN PATENT DOCUMENTS

| | | |
|---|---|---|
| EP | 1857063 A1 | 11/2007 |
| FR | 2 749 499 | 12/1997 |
| WO | 2007/067297 | 6/2007 |

OTHER PUBLICATIONS

International Search Report and Written Opinion dated Sep. 27, 2012 from counterpart PCT/IB2012/052955.

(Continued)

*Primary Examiner* — Pedro Philogene
*Assistant Examiner* — Lynnsy Summitt
(74) *Attorney, Agent, or Firm* — Timothy J. Klima; Shuttleworth & Ingersoll, PLC

(57) ABSTRACT

A device for the external fixation of a first bone element and a second bone element articulated to each other, comprises: a guide member equipped with a curvilinear guide; a first fastening member slidably associated with the guide and equipped with first means for releasable fastening to the first bone element; a second fastening member associated with the guide member and equipped with first means for releasable fastening to the second bone element; and relative movement means by which the first fastening member is moved relative to the second fastening member along the guide.

16 Claims, 8 Drawing Sheets

(56) References Cited

U.S. PATENT DOCUMENTS

| | | | |
|---|---|---|---|
| 4,978,348 A | 12/1990 | Ilizarov | |
| 4,988,349 A * | 1/1991 | Pennig | A61B 17/6416 606/57 |
| 5,382,248 A | 1/1995 | Jacobson et al. | |
| 6,179,846 B1 * | 1/2001 | McFadden | A61B 19/203 602/37 |
| 8,702,713 B2 * | 4/2014 | Nayet | A61B 17/708 606/86 A |
| 2005/0251135 A1 | 11/2005 | Riccione et al. | |
| 2006/0122606 A1 * | 6/2006 | Wolgen | A61B 17/663 606/71 |
| 2007/0043370 A1 * | 2/2007 | Ueda | A61B 17/663 606/71 |

OTHER PUBLICATIONS

European Search Report dated Feb. 1, 2012 from counterpart App No. IT BO20110370.

* cited by examiner

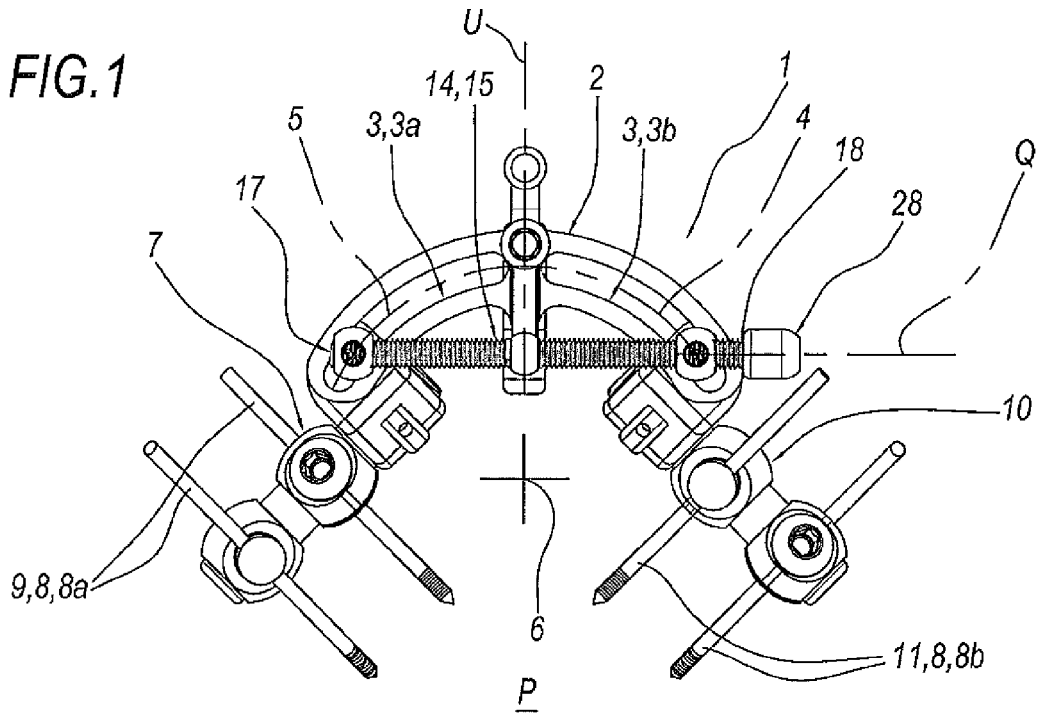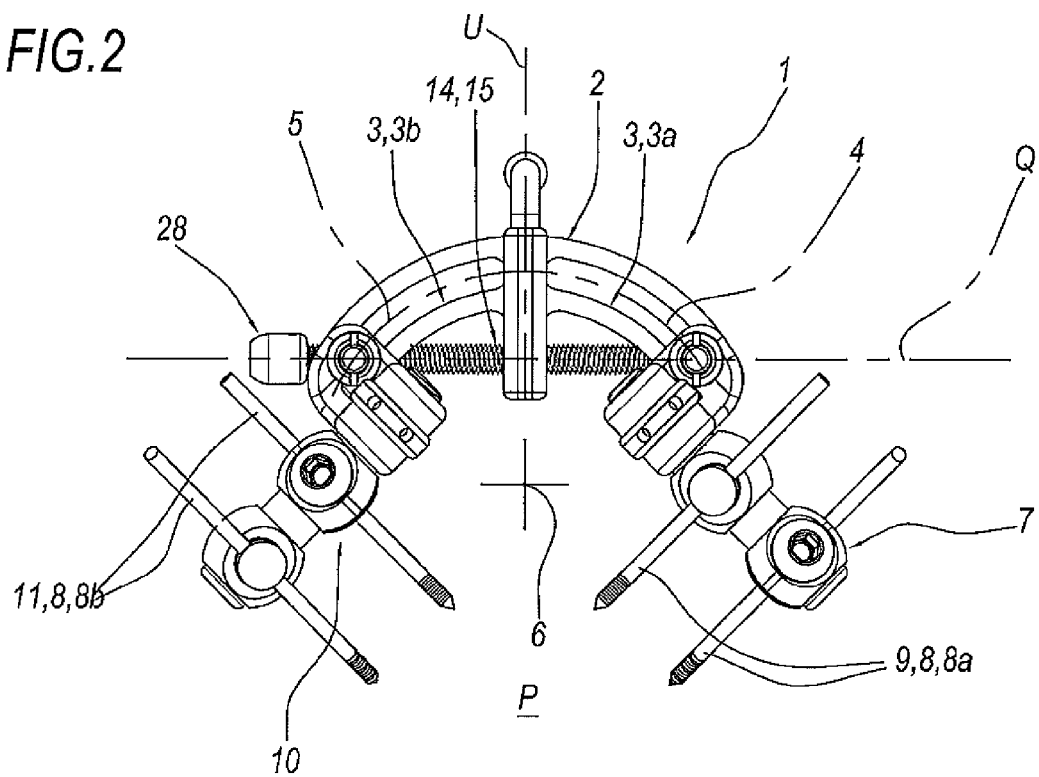

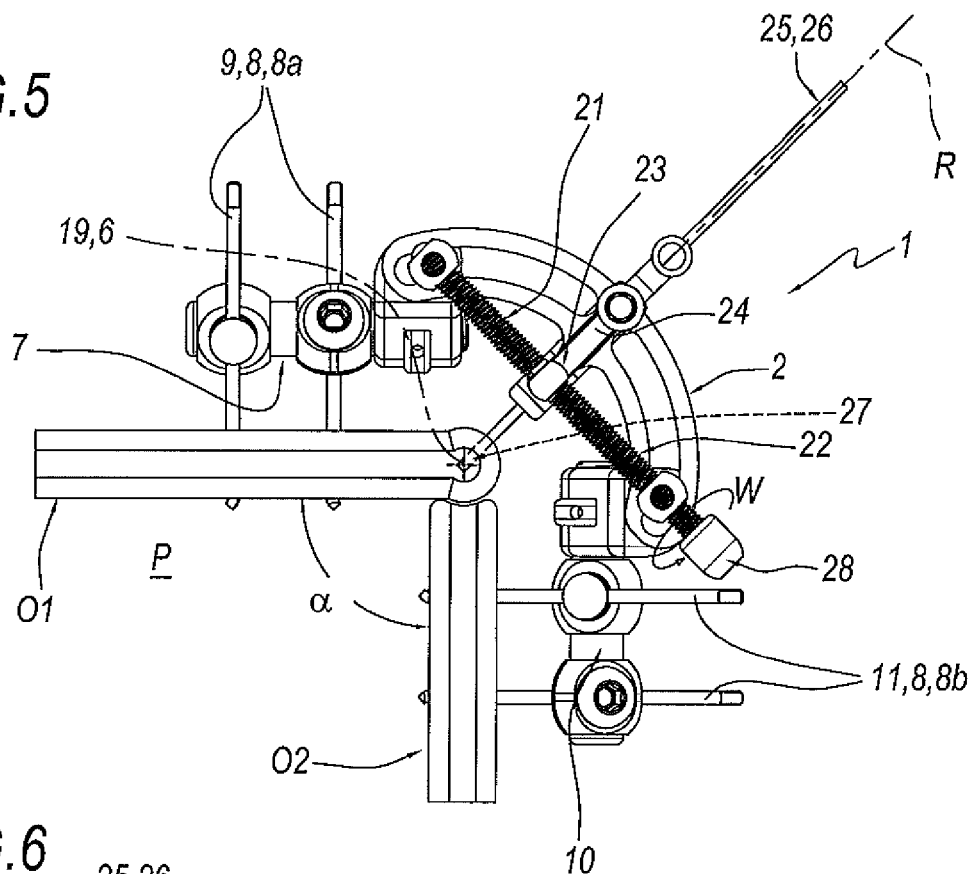
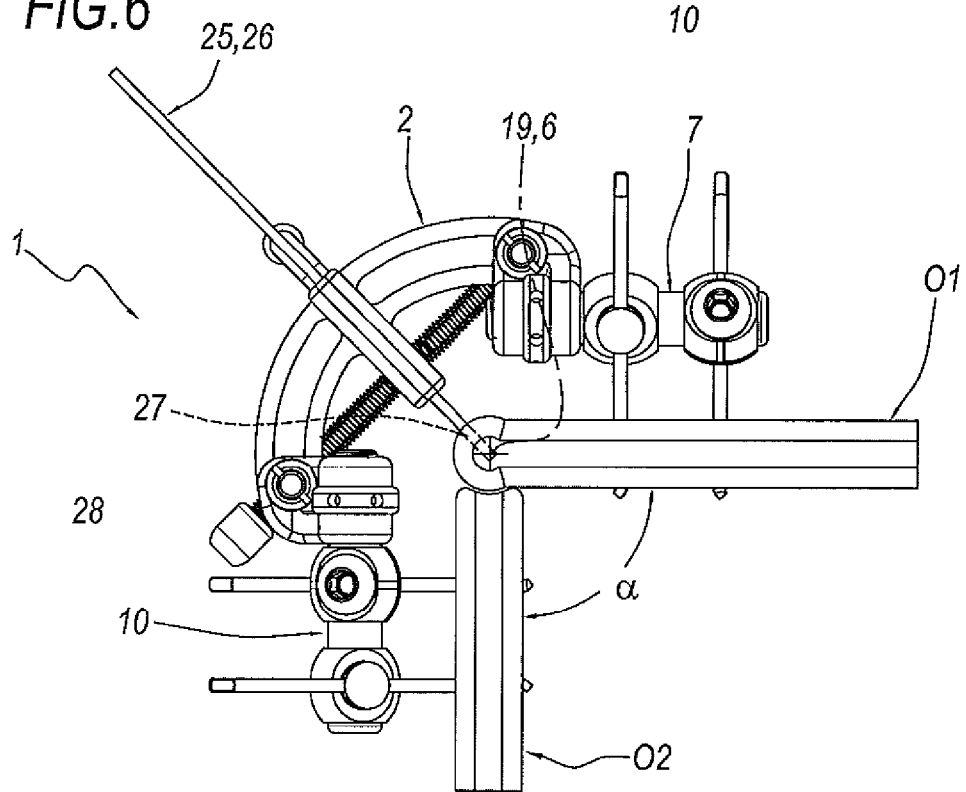

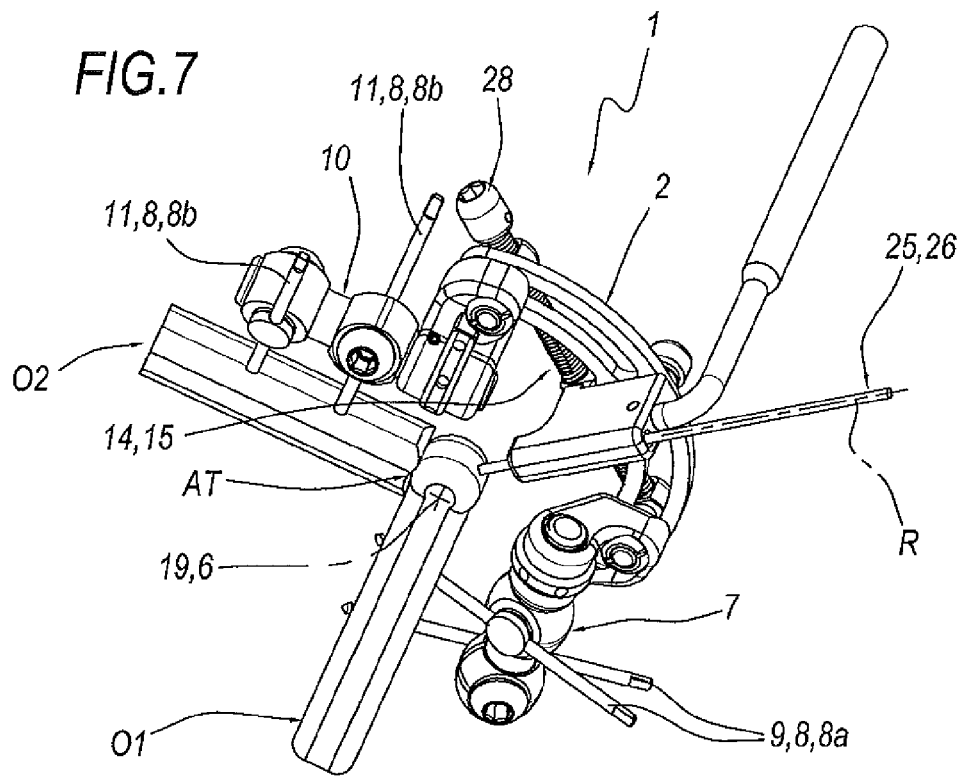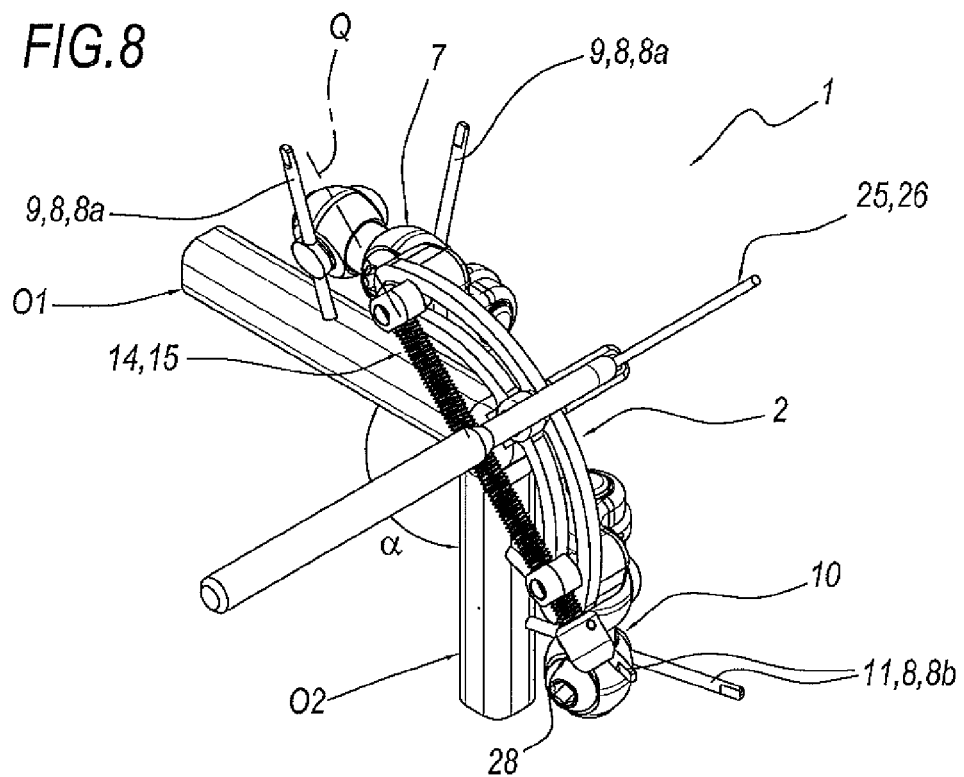

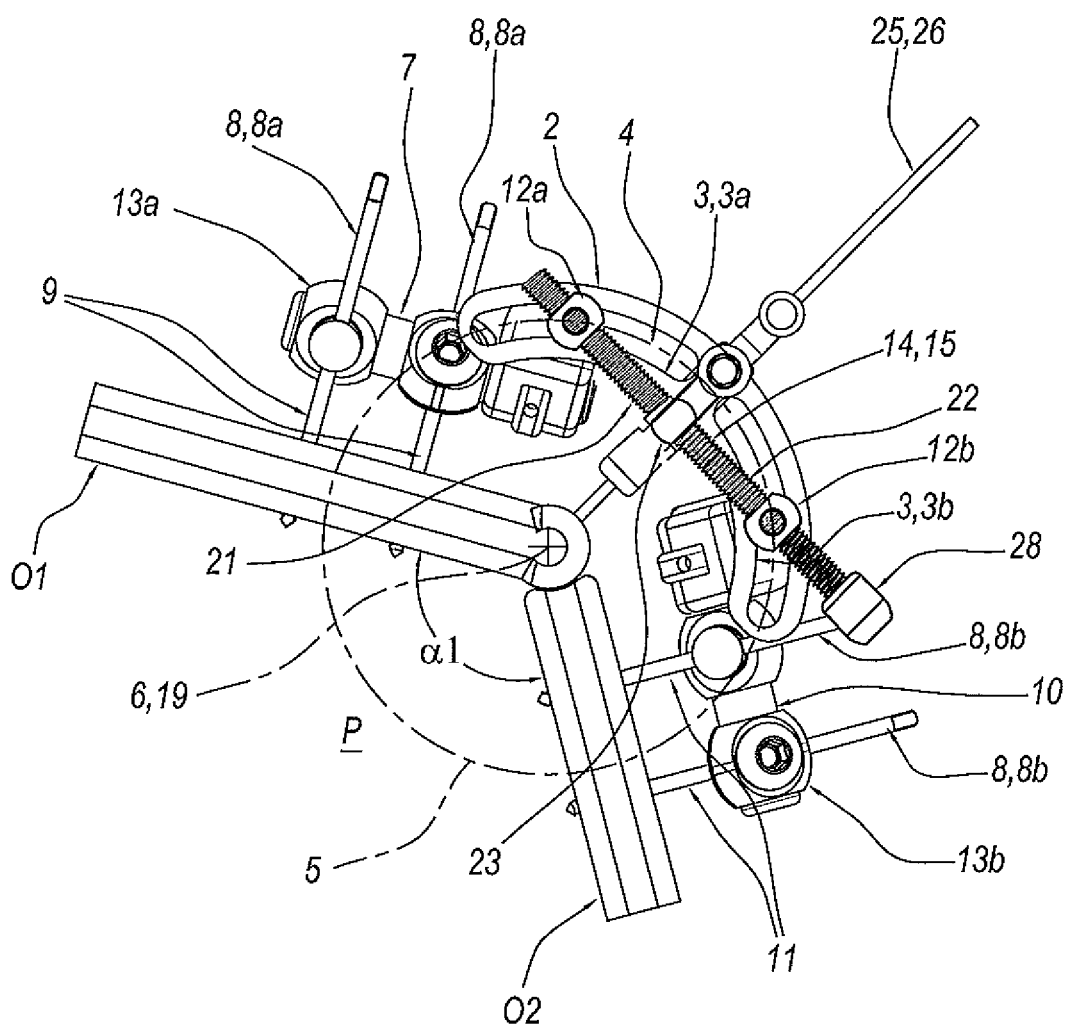

EXTERNAL FIXATION DEVICE

This application is the National Phase of International Application PCT/IB2012/052955 filed Jun. 12, 2012 which designated the U.S. and that International Application was published under PCT Article 21(2) in English.

This application claims priority to Italian Patent Application No. BO2011A000370 filed Jun. 27, 2011, which application is incorporated by reference herein.

TECHNICAL FIELD

This invention relates to a device for the external fixation of bone articulations, in particular for, but not limited to, the finger articulations of a hand.

BACKGROUND ART

In a well-known progressive disease involving the flexor tendon of an articulation (in particular, the articulation of one of the fingers of a hand), the flexor tendon becomes progressively shorter, thus reducing, and eventually totally preventing, the possibility of movement of the bone elements which are connected by the articulation.

When the disease reaches an advanced stage, the two bone elements are angularly locked to each other, without any possibility of relative movement because the tendon is contracted and no longer able to extend.

Under these circumstances, to date, surgery can be performed with difficulty and gives uncertain results.

Indeed, it should be noted that the surgical operation means that the flexor tendon must be returned to the non-contracted position (where the two bone elements defining the articulation are substantially parallel to each other).

According to the current state of the art, to return the flexor tendon to its non-contracted configuration, the specialist surgeon uses devices equipped with elastic attachments which make it possible to apply traction to the two articulated bone elements. These devices, however, are relatively ineffective and, in particular, imprecise. The risk, therefore is that of incorrectly deforming the bone elements or incorrectly lengthening the tendons connecting the bone elements.

Moreover, these devices are often particularly cumbersome and cannot therefore be applied to all the joints of the human body (such as, for example, the bone elements of the middle finger).

Another strongly felt need in the orthopaedic field is that for a device that can be used to correctly restore the bone structure after a trauma.

For example, it is frequent for one or more bones not to set properly as a result of incorrect treatment of an injury.

DISCLOSURE OF THE INVENTION

The aim of the present invention is, therefore, to overcome these disadvantages by providing an external fixation device for bone elements.

According to the invention, this aim is achieved by an external fixation device comprising the technical features described in one or more of the appended claims.

BRIEF DESCRIPTION OF THE DRAWINGS

The technical features of the invention, with reference to the above aims, are clearly described in the claims below and its advantages are more apparent from the detailed description which follows, with reference to the accompanying drawings, which illustrate a preferred, non-limiting example embodiment of the invention, and in which:

FIG. 1 is a front view of a preferred embodiment of the fixation device of the invention;

FIG. 2 is a rear view of a preferred embodiment of the fixation device of the invention;

FIG. 5 is a front view of the fixation device of FIGS. 1-4 applied to a pair of articulated bone elements;

FIG. 6 is a rear view of the fixation device of FIG. 5;

FIGS. 7 and 8 ere perspective views of the fixation device of FIGS. 5 and 6, respectively;

FIG. 9 illustrates the device of FIG. 5 in another configuration;

DETAILED DESCRIPTION OF THE PREFERRED EMBODIMENTS OF THE INVENTION

Figure 3:
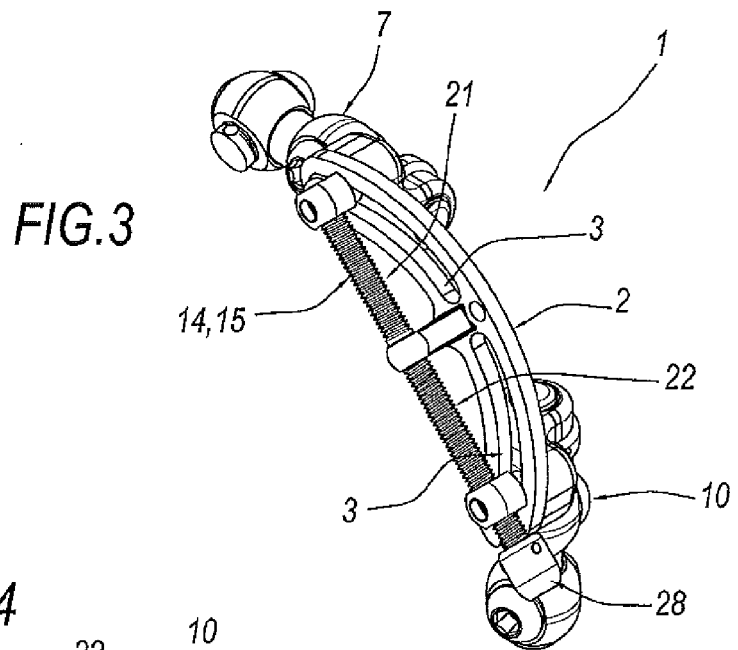
FIG. 3 is a perspective view of the fixation device of FIGS. 1 and 2.

With reference to the accompanying drawings, the numeral 1 denotes an external fixation device for a first bone element O1 and a second bone element O2 which are articulated (rotatably coupled) to each other.

By "articulated bone elements" is also meant bone elements O1 and O2 between which two or more articulations are interposed. For example, the metacarpus of the hand and the second phalanx of a finger are bone elements O1 and O2 which are articulated to each other.

It should be noted that the term "fixation device" is used to denote an orthopaedic device 1 configured to connect two bone elements O1 and O2 independently of one another in such a way as to allow fixation, lengthening and/or relative movement of the bone elements.

The device is designed to be located outside the patient's body, that is to say, it is an external device.

The bone elements O1 and O2 are bone elements of a patient's body.

It should be noted that the bone elements O1 and O2 are connected to each other by an articulation AT.

More specifically, the bone elements O1 and O2 can rotate (in one plane)—relative to one another—about a centre of rotation, which is denoted by the reference numeral 19.

The device 1, clearly shown in FIG. 1, comprises a guide element 2, hereinafter referred also to as guide member 2, equipped with a curvilinear guide 3.

It should be noted that the curvilinear guide 3 extends in a plane P.

In the embodiment illustrated, the guide 3 has the shape of an arc 4 of a circle 5.

The circle 5 has a predetermined curvature radius and a centre 6.

It should be noted that, according to the invention, the device 1 comprises a first fastening member 7 slidably associated with the guide 3 of the guide member 2.

Figure 4:
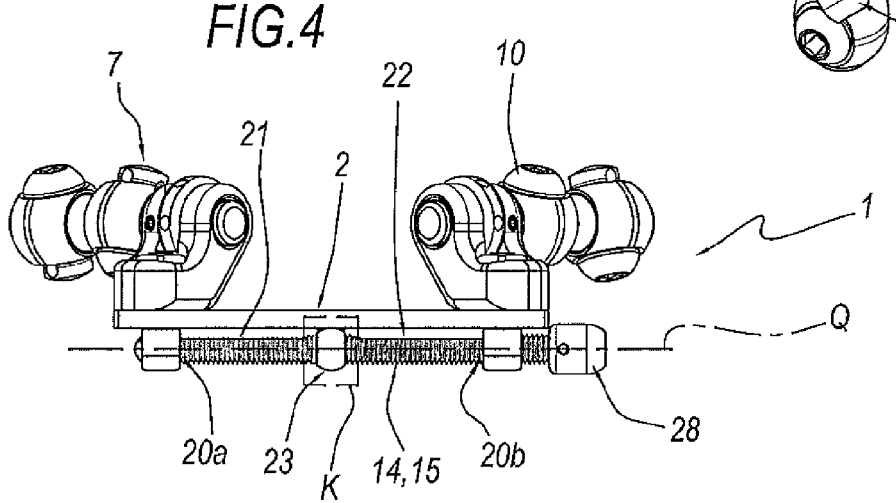
FIG. 4 is a plan view of the fixation device of FIGS. 1 and 2.
Figure 4A:
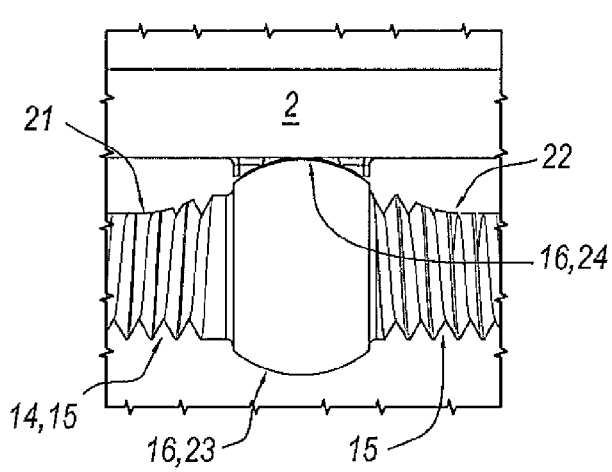
FIG. 4a is a plan view of a detail K from FIG. 4.
Figure 4B:
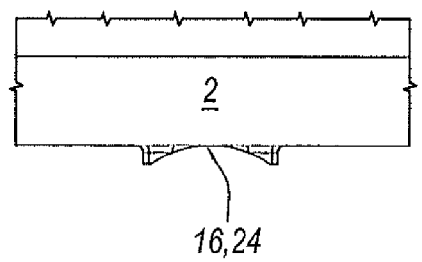
FIG. 4b is a plan view of the detail of FIG. 4a, with some parts cut away in order to better illustrate others.

The first fastening member 7 comprises a pair 8a of threaded pins 8 (illustrated in all the accompanying drawings except FIGS. 3 and 4), configured to be inserted into the first bone element O1 and to cause the first fastening member 7 to be locked relative to the first bone element O1

Hence, more generally speaking, the threaded pins 8 define fastening means 9, configured for releasable fastening of the first fastening member 7 to the first bone element O1.

The device 1 also comprises a second fastening member 10 associated with the guide member 2.

In the embodiment illustrated, the second fastening member 10 comprises a pair 8b of threaded pins 8 (illustrated in all the accompanying drawings except FIGS. 3 and 4), configured to be inserted into the second bone element O2.

These threaded pins 8 define second fastening means 11 configured for releasable fastening of the second fastening member 10 to the second bone element O2 and to cause the second fastening member 10 to be locked relative to the second bone element O2.

Hereinafter, the first fastening member 7 is described in detail. With reference in particular to FIGS. 1 to 9, the second fastening member 10 has the same technical features as the first fastening member 7 and thus, the considerations set out with regard to the first fastening member 7 also apply to the second fastening member 10.

The first fastening member 7 comprises two portions 12a, 13a connected to each other as one.

One of these portions, hereinafter referred to as first portion 12a, is coupled to the guide 3, that is, it is slidably associated with the guide 3 itself.

Another 13a of these portions, hereinafter referred to as second portion 13a, mounts the fastening means 9 by which the fastening member 7 is fixed to the bone element O1.

According to the invention, the device 1 comprises means 14 for moving the first fastening member 7 relative to the second fastening member 10.

The movement means 14 allow the first and second fastening members 7, 10 to move relative to each other.

Preferably, the movement means 14 by which the first fastening member 7 is moved relative to the second fastening member 10 operate on the first fastening member 7 and on the second fastening member 10.

According to a preferred, non-limiting embodiment, the movement means 14 comprise:

an at least partly threaded element 15 screwed to at least one of the fastening members 7, 10 and designed to be driven in rotation in such a way as to move the fastening members 7, 10 relative to each other; and means 16 for guiding the element and configured to guide the element 15 relative to the guide member 2 in such a way as to centre it.

In the preferred embodiment illustrated, but not limited to it, the threaded element 15 is screwed to the first fastening member 7 and to the second fastening member 10.

More specifically, the threaded element 15 is screwed, at a first end of it 17, to the first portion 12a of the first fastening member 7 and, at a second end of it 18, to the first portion 12b of the second fastening member 10.

It should be noted that the first fastening member 7 and the second fastening member 10 comprise threaded holes 20a, 20b configured to screwably receive the threaded element 15.

It should be noted that the coupling created between each fastening member 7, 10 and the threaded element 15 is a lead nut and screw mechanism.

More specifically, in the embodiment illustrated, the element 15 comprises a first portion 21 having left-handed threading configured to screwably engage in the hole 20a of the first fastening member 7 and a second portion 22 having right-handed threading configured to screwably engage in the hole 20b of the second fastening member 10.

It should be noted that the threaded element 15 centrally bears a bushing 23.

The term bushing means a portion which is radially enlarged relative to the element 15.

The bushing 23 is rigidly connected, preferably welded, to the threaded element 15.

It should be noted that the guide member 2 has formed in it a guide socket 24 for the bushing 23 configured to guide the bushing 23 along a predetermined movement direction U.

The bushing 23 and the guide socket 24 define guide means 16 for the threaded element 15, configured to guide the threaded element 15 relative to the guide member 2.

FIGS. 5 to 9 illustrate a positioning device 25—associated with the device 1—to allow the device 1 to be correctly positioned relative to the articulation AT of the bone elements O1, O2 the device 1 itself is applied to, and in particular to centre the device 1 relative to the centre of rotation 19 of the bone elements O1, O2.

The device 1 and the positioning device 25 together define an assembly of elements acting in conjunction with each other.

The positioning device 25 comprises a rod 26 (or positioning element 26), called "wire" in the jargon of the trade, which is slidable relative to the guide member 2 along a direction of movement R passing through the centre of curvature 6 of the guide 3 and lying in the plane P.

The rod 26 is configured to be inserted into the patient's body until reaching the centre 19 of the articulation AT of the two bone elements O1, O2.

Described below is the use of the device 1, with reference to the application of the device 1 to a first and a second bone element O1, O2 which are connected to each other by an articulation AT, that is, which are hinged to each other with the possibility of rotating in one plane P.

The rod 26 is inserted into the patient's body until one end 27 of the rod 26 reaches the centre 19 of the articulation AT.

It should be noted that customary X-ray instruments are used to check that the end 27 of the rod 26 is positioned exactly at the centre 19 of the articulation (corresponding to the centre of rotation of the two bone elements O1 and O2).

The guide member 2 is placed in a predetermined position relative to the rod 26, in such a way that the centre of curvature 6 of the guide 3 coincides with the centre of rotation 19 of the two bone elements O1, O2.

The predetermined position of the device 1 relative to the rod 26 depends on the radius of curvature of the guide 3. Indeed, the greater the radius of curvature is, the further the position of the device 1 from the end 27 of the rod 26 (which, as stated above, is placed at the centre of rotation 19 of the two bone elements O1 and O2).

It should be noted that at the position thus defined the threaded pins 8 of the first and second fastening members 7 and 10 are screwed to the respective bone elements O1, O2, in such a way as to firmly lock the fastening members 7 and 10 (and more in general, the device 1) relative to the bone elements O1 and O2.

Once the device 1 has been fastened to the bone elements O1 and O2 in the manner described above, the rod 26 can be removed from the patient's body.

The device 1 allows the two bone elements O1 and O2 to be set at a predetermined angle to each other, that is, it allows the patient or medical operator to check the angle of opening of the articulation (labelled α in the accompanying drawings).

FIGS. 5 and 9 show two different configurations of the device 1, namely a first configuration (FIG. 5) where the two bone elements O1 and O2 are set at right angles; and a second configuration (FIG. 9) where the two bone elements O1 and O2 are set in such a way as to form, in the articulation, an angle of opening α1 which is greater than 90°.

Starting from the configuration illustrated in FIG. 5, the patient or medical operator turns the threaded element 15 to adjust the angle of opening a of the articulation (more specifically, the user turns the element 15 by acting on the ring nut 28).

Preferably, the element 15 is configured to turn by discrete steps (that is, by substantially constant angular steps). This allows the user to control the adjustment more easily.

Thanks to the lead nut and screw couplings between the element 15 and the fastening members 7 and 10, turning the element 15 in the direction labelled W causes a force directed along the axis of the element 15 to be applied to the fastening members 7 and 10 (the direction labelled Q) towards the bushing 23.

The two fastening member 7, 10 are thus drawn together along the direction Q. It should be noted that the fastening members move in the guide 3.

Thanks to the forces exchanged between the guide 3 and the first portion 12a, 12b of each fastening member 7, 10 and between the bushing 23 and the walls of the socket 24 which houses the bushing 23, turning the element 15 not only causes displacement of the fastening members 7, 10 along the guide 3 but also translation of the threaded element 15 relative to the guide member 2 in the direction of movement labelled U.

Thus, while the fastening members 7, 10 are displaced along the guide 3 (in such a way as to vary their distance from each other along the direction of extension Q of the element 15), the element 15 is itself displaced relative to the guide member along the direction U (in practice, remaining parallel).

It should therefore be noted that according to the invention, the relative movement means 14 produce relative translation of the fastening members 7, 10 along the guide 3.

FIG. 9 shows a different configuration of the device 1.

As may be observed in FIG. 9, both of the fastening members 7, 10 are located at a different position along the guide 3 from that shown in FIG. 5.

More specifically, each position of the fastening members 7, 10 along the guide 3 corresponds to a specific angle of opening of the articulation AT of the bone elements O1 and O2.

What is described is normally performed daily by the patient to modify the angle of opening α of the articulation AT of the two bone elements O1, O2 according to the therapy instructions provided by the medical operator.

This advantageously allows treatment of certain degenerative diseases of the tendons or of bone disorders resulting from traumas.

With regard to the threaded element 15, attention is drawn to the following.

Preferably, the threading of the element 15 (left-handed and right-handed) has a helix angle which is such as to prevent any unwanted relative displacement of the two fastening members 7, 10. In other words, the helix angle of the threading is just a few degrees; so as to prevent—during normal use of the device 1—the spontaneous unscrewing of the element 15, which would lead to unwanted movement of the relative position of the two fastening members 7, 10 along the guide 3 (that is to say, would lead to unwanted movement of the two bone elements O1 and O2).

Thus, the element 15 preferably comprises a fine-pitch thread.

An advantage of the invention is that it allows the angle of opening α of the articulation of the two bone elements O2, O1 to be adjusted in an extremely precise and simple manner.

That means patients themselves can perform the therapy of certain bone disorders or traumas independently, without requiring the intervention of the specialist.

Another advantage of the device 1 is that it is extremely compact and can be used for the fixation of any articulated bone element: indeed, it should be noted that wherever the device 1 is applied, the guide member 2 and the fastening members 7, 10 are, in use, positioned in the plane P of rotation of the bone elements and protrude from the patient's body without interfering either with these bone elements or with other bone elements.

Below are some general considerations regarding the device 1.

It should be noted that for the purposes of the invention, even just one of the two fastening members 7, 10 may be movable relative to the guide 3 (that is, relative to the guide member 2).

Thus, in a variant which is not illustrated, one of the two fastening members 7, 10 is associated with (fixedly attached to) the guide 3 while the other of the two fastening members is slidably associated with the guide 3

It should be noted that the relative movement means 14 of the fastening members 7, 10 might also be of a different type.

With regard to the means 14 for moving the first fastening member 7 relative to the second fastening member 10, attention is drawn to the following.

More generally speaking, the relative movement means 14 allow the user to move the two fastening members 7, 10 relatively (thus, relative to the guide 3, they may be configured to allow movement of one or both of the fastening members 7 and 10).

Generally speaking, according to the invention, the relative movement means 14 of the fastening members 7, 10 can be configured according to any of the alternatives listed below:

i) the means 14 operate on any one of the fastening member, to allow movement of just one of the fastening members relative to the guide member;

ii) the movement means operate simultaneously on both of the fastening members (as in the preferred embodiment illustrated in the accompanying drawings);

iii) the movement means operate on both of the fastening members individually and independently.

With regard to the guide 3, attention is drawn to the following.

In the embodiment illustrated, the guide 3 is in the form of a slot made in the guide member 2.

More specifically, the guide 3 is in the form of a pair of slots, namely, a first slot 3a in which the first fastening member 7 is slidably inserted, and a second slot 3b in which the second fastening member 10 is slidably inserted.

It should be noted therefore that a portion of the first fastening member 7 and of the second fastening member 10 is inserted in the respective slot in such a way as to be slidable therein (and also in such a way that it cannot be pulled out of the slot).

In a variant which is not illustrated, the guide 3 has a curvilinear configuration (with a variable curvature radius).

According to this variant, the guide 3 may be configured to produce rotation of the bone elements about the centre 19 and traction of the bone elements themselves (that is, in such a way as to apply a traction force on the bone elements O1 and O2 along the main direction of extension of the bone elements O1 and O2 themselves).

For the purpose, the guide 3 is shaped to produce a suitable movement of one or both of the fastening members along the curvilinear path defined by the guide 3 itself.

It should be noted that the device 1 may also be used on bone segments O1, O2 which are not articulated to each other.

Such segments might, for example, form part of the same bone separated by osteotomy or accidental fracture.

According to this aspect, the first fastening member is connected to a first bone segment and the second fastening member is connected to a second bone segment.

in that case. advantageously, the device 1 allows correction of the relative position between the bone segments so as to set them at the right angle to each other.

Figure 10:
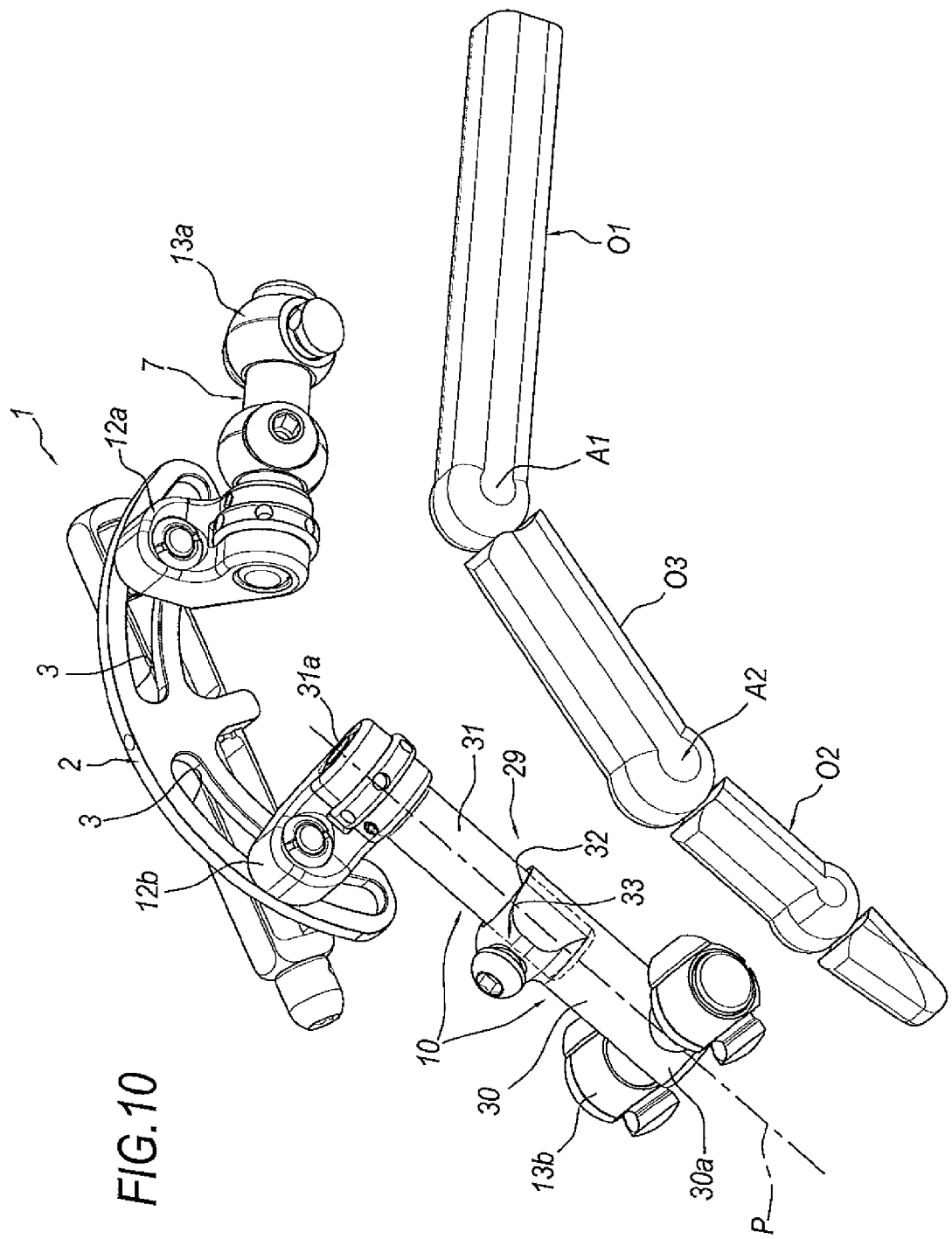
FIG. 10 is a perspective view of a second embodiment of the fixation device according to the invention.

FIG. 10 shows a second embodiment of the device 1.

The second embodiment of the device 1 is used in particular for lengthening articulated bone elements O1 and O2 with two or more articulations interposed between them.

More specifically, in the embodiment illustrated, there is a bone element O3 interposed between the bone elements O1 and O2.

The bone element O3 is connected to both of the bone elements O1 and O2 by a respective articulation.

More precisely, a first articulation A1 connects the bone elements O1 and O3 and a second articulation A2 connects the bone elements O2 and O3.

The bone elements O1, O2 and O3 can rotate relative to each other about the first and the second articulation A1 and A2 defining a first and a second centre of rotation 34 and 35, respectively.

The second embodiment of the device 1 differs from the device 1 described previously in that the second fastening member 10 comprises linear movement means 29, whilst the first fastening member 7 has the same features as those described previously and denoted hereinafter by the same reference labels.

As described above, the second fastening member 10 comprises a first and a second portion 12b, 13b. The first portion 12b is coupled to the guide 3 and the second portion 13b comprises the second means 11 for fastening the second fastening member 10 to the bone element O2. The threaded pins 8 define the second fastening means 11.

The linear movement means 29 of the second fastening member 10 comprise a slider 30 slidably associated with a shaft 31 in such a way as to translate along the shaft 31 itself.

The slider 30 and the shaft 31 respectively define a movable member and a guide member of the linear movement means 29.

The shaft 31 is cylindrical in shape, with a longitudinal main axis of extension P.

The slider 30 is substantially cylindrical in shape, extending mainly along the longitudinal axis P, and has a cavity 32 in it.

More specifically, the cavity 32, whose shape is substantially cylindrical along the longitudinal axis P, is a blind cavity.

More precisely, the inside surface of the cavity 32 is shaped to match the outside surface of the shaft 31, so the two fit together.

The inside surface of the cavity 32 and the outside surface of the guide member 31 fit together with clearance in such a way as to allow the slider 30 to slide freely along the shaft 31.

The linear movement means 29 connect the first and the second portion 12b, 13b of the second fastening member 10 in such a way as to allow movement of the second portion 13b relative to the first portion 12b, during activation (adjustment) of the means 14 for moving the first fastening member 7 relative to the second fastening member 10 along the guide 3.

More precisely, the shaft 31 is coupled to the first portion 12b and the slider 30 is coupled to the second portion 13b.

One end 31a of the shaft 31 is conected to the first portion 12b. The end 31a is at least partly threaded and the first portion 12b has a threaded hole configured to screwably receive the end 31a in such a way as to create a lead nut and screw coupling.

Preferably, the second portion 131D is located at one end 30a of the slider 30. This end is opposite the end 31a of the shaft 31.

The linear movement means 29 comprise a fastening screw 33 for setting the slider 30 relative to the shaft 31. More specifically, the fastening screw 33 prevents movement of the slider 30 relative to the shaft 31, defining a means for locking the slider 30 to the shaft 31.

The fastening screw 33 can be acted upon by an operator.

Advantageously, when the pins 8 of the second fastening member 10 are inserted into the second bone element O2, the slider 30 is connected as one with the shaft 31 by screwing in the screw 33.

Once the pins 8 have been inserted into the second bone element O2, the slider 30 can be left free to slide on the shaft 31 by slackening the screw 33.

In the embodiment illustrated, the fixation device 1 is fastened to the bone elements O1 and O2, which are articulated to each other, in such a way that the centre of curvature 6 of the guide 3 is interposed between the two centres of rotation 34 and 35.

More precisely, the fixation device 1 is positioned in such a way that the centre of curvature 6 of the guide 3 is located at, or in the proximity of, the centre of instantaneous rotation l of the bone element O2 and of the bone element O1.

Figure 11:
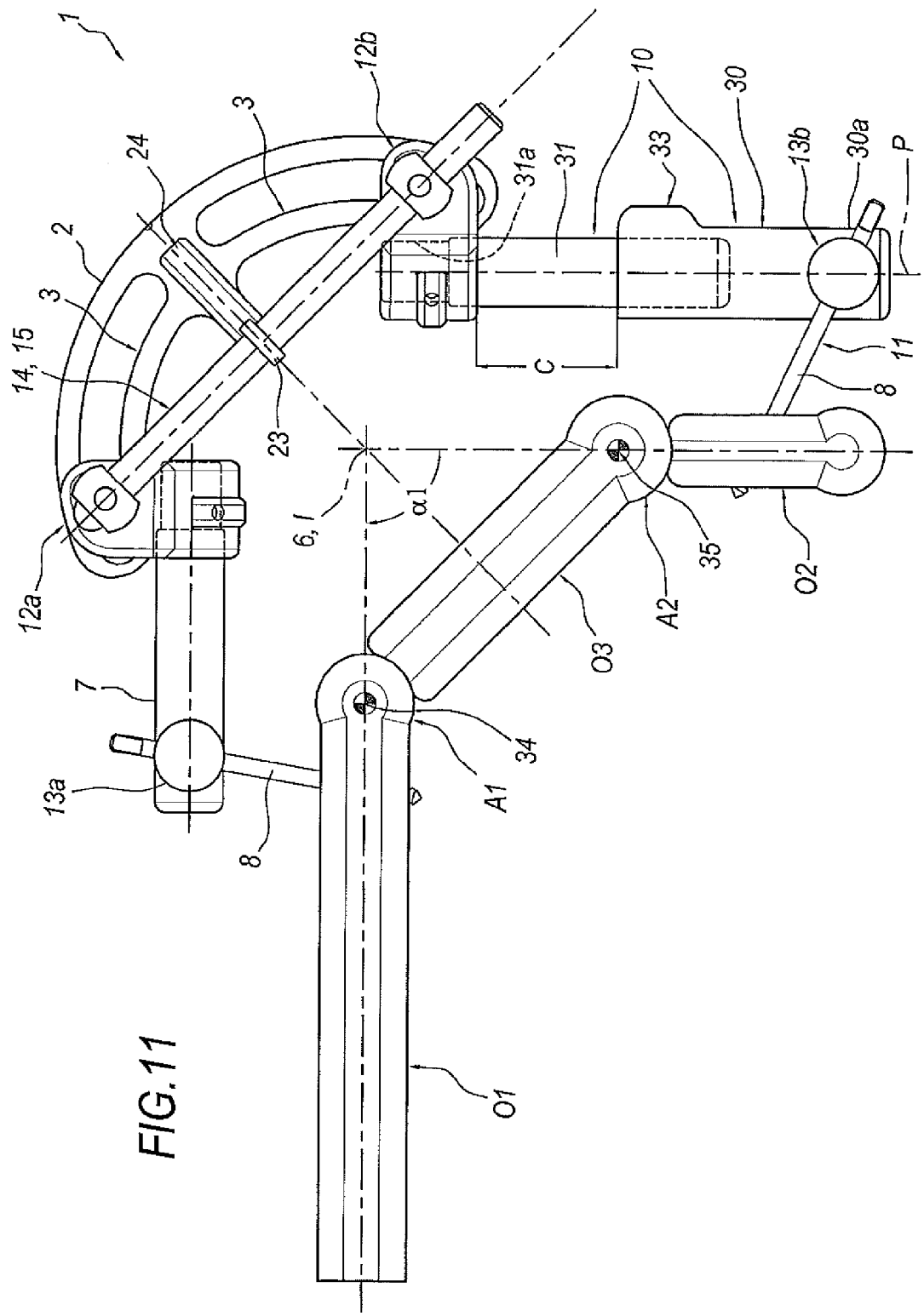
FIG. 11 is a front view of a first configuration of he fixation device of FIG. 10.
Figure 12:
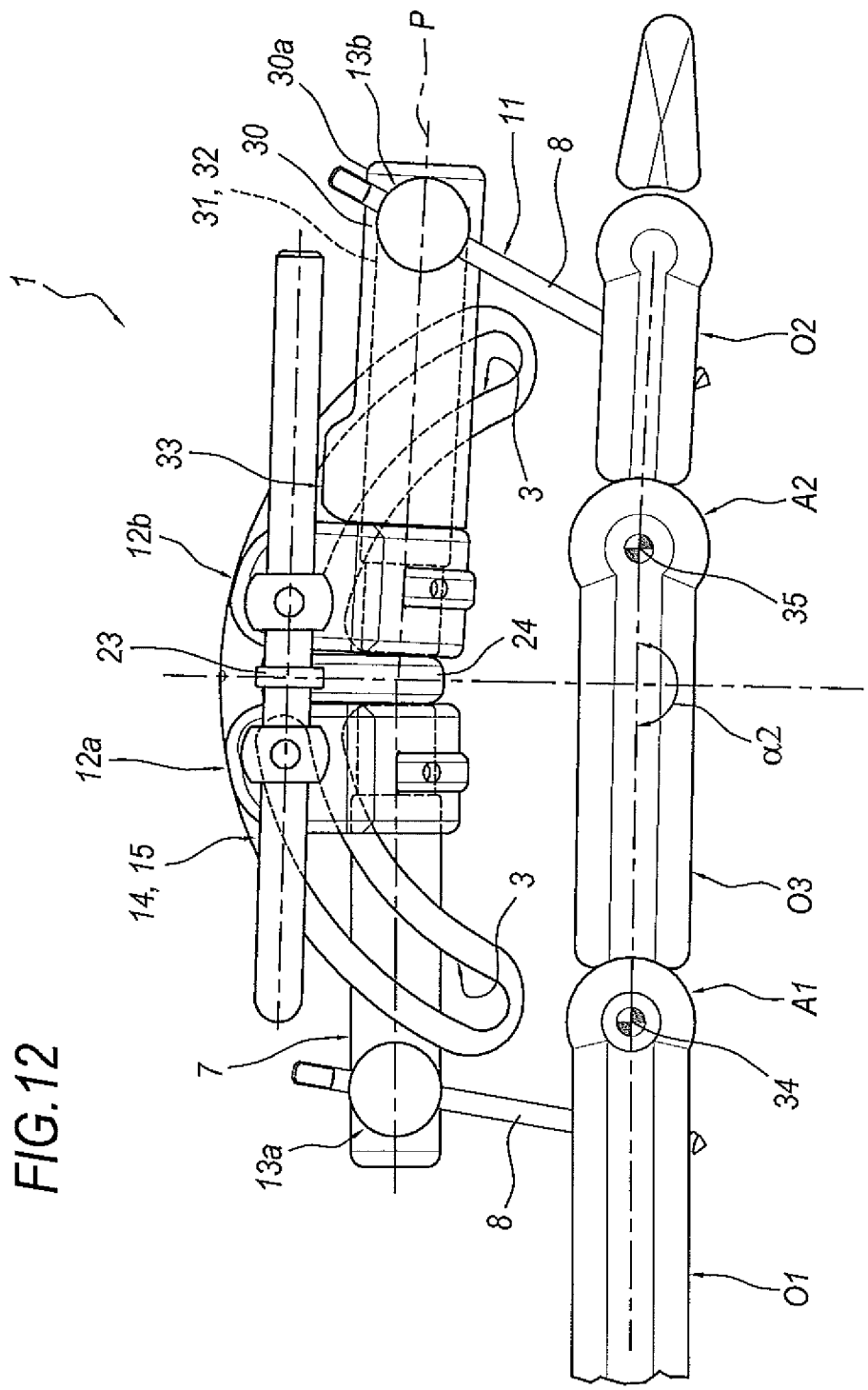
FIG. 12 is a front view of a second configuration of the fixation device of FIG. 10.

FIGS. 11 and 12 illustrate two different configurations of the device 1 fastened to the bone elements O1 and O2: a first configuration (FIG. 11) where the two bone elements O1 and O2 are set in such a way as to form an angle of opening α1; and a second configuration (FIG. 12) where the two bone elements O1 and O2 are set in such a way as to form an angle of opening α2 which is greater than α1.

FIG. 11 shows an angle of opening α1 of 90°, whilst the angle of opening α2 shown in FIG. 12 is 180°.

The first and second configurations described and illustrated here are configurations given purely by way of example, since the angles of opening α1 and α2 may vary according to the patient's medical conditions and therapy instructions.

The bone element O3, on the other hand, is set at an angle of approximately 45° to the bone elements O1 and O2 in the first configuration and, in the second configuration, is substantially aligned with the bone elements O1 and O2.

In the first configuration, illustrated in FIG. 11, the slider 30 of the device 1 is at a position furthest away from the second portion 12b.

It should be noted that in this configuration, the bushing 23 is located at the lower end of the guide 24 and, consequently, the first and second fastening members 7 and 10 are positioned near one of the ends of the respective guide 3

In the second configuration of the device 1, illustrated in FIG. 12, the slider 30 is at the position closest to the second portion 12b. In this configuration, the bushing 23 is located at the upper end of the guide 24 and, consequently, the first and second fastening members 7 and 10 are positioned near one of the ends of the respective guide 3

More precisely, the slider 30 has a working stroke, labelled C, whose length is defined by the two end positions of the slider 30 relative to the shaft 31. More specifically, the length is defined by the position where the slider 30 is furthest away from the first portion 12b and by the position where the slider 30 is closest to and in abutment with the first portion 12b.

Starting from the first configuration illustrated in FIG. 11, the patient or medical operator turns the threaded element 15.

Turning the threaded element 15 as described previously causes the fastening members 7, 10 to be drawn together along the guide 3.

The displacement of the fastening members 7, 10 causes the simultaneous rotation of the bone elements O3 and O2 about the centres of rotation 34 and 35.

During rotation of the bone element O3 about the centre of rotation 34, the bone element O1 holds its position relative to the centre of rotation 34.

While the bone elements O3 and O2 rotate about the two centres of rotation 34 and 35, that is, about the first and second articulations A1 and A2, the fastening members 7, 10 rotate about a single centre of rotation 6. Consequently, the trajectory followed by the bone elements O2 and O3 is different from the trajectory followed by the fastening members 7, 10.

This difference is in practice compensated by the linear movement means 29, thanks to the translation of the slider 30 along the shaft 31, along a direction parallel to the direction of the axis P.

More precisely, the trajectory followed by the bone element O2 as a result of rotation of the bone element O2 itself about the two centres of rotation 34, 35, is in practice reproduced by the simultaneous translation of the slider 30 along the shaft 31 and by the rotation of the second fastening member about the centre of curvature 6 of the guide 3.

It should be noted that the compensation obtained by the linear movement means 29, that is, by the translation of the slider 30 along the shaft 31, depends on how much the rotation of the second fastening member 10 deviates from the rotation of the bone elements O3 and O2 about the respective centres of rotation 34, 35.

In practice, the advancement of the slider 30 along the shaft 31 is variable during the course of therapy since the movable member 30 translates by just so much as necessary to compensate for the differences in the aforementioned trajectories.

The full working stroke C can be obtained by summing the spaces travelled by the slider 30, during the passage from the first configuration to the second configuration of the device 1.

Lastly, it should be noted that during translation of the slider 30 as it travels the length of the working stroke C, the bushing 23 simultaneously travels the guide 24, from its lower end towards its upper end.

Advantageously, the device 1 makes it possible to stretch the bone elements O1, O2 and O3, connected to each other by two interposed articulations A1 and A2, starting from a first configuration, where the two bone elements O1 and O2 are substantially at right angles to each other, until reaching a second configuration where the two bone elements O1 and O2 are substantially aligned.

Lastly, it should be noted that the positioning device 25 allows the device 1 to be positioned correctly relative to the articulated bone elements O1, O3 and O2. More specifically, the positioning device 25 allows the device 1 to be centred about the centre of instantaneous rotation I of the bone elements O1 and O2.

According to what is described above, the device 1 can be used to lengthen the bone elements O1 and O2, for the treatment of certain diseases.

The invention described is susceptible of industrial application and may be modified and adapted in several ways without thereby departing from the scope of the inventive concept. Moreover, all details of the invention may be substituted by technically equivalent elements.

The invention claimed is:

1. A device for external fixation of a first bone element and a second bone element articulated to each other, comprising:
    a guide member equipped with a curvilinear guide;
    a first fastening member slidably associated with the curvilinear guide and equipped with first means for releasable fastening to the first bone element;
    a second fastening member associated with the curvilinear guide and equipped with second means for releasable fastening to the second bone element, the second fastening member being slidably associated with the curvilinear guide; and
    relative movement means by which the first fastening member is moved relative to the second fastening member along the curvilinear guide, wherein the relative movement means are configured to operate simultaneously on both the first fastening member and on the second fastening member in such a way as to move the first fastening member and the second fastening member along the curvilinear guide, the relative movement means comprising an at least partly threaded element screwed at least to the first fastening member to define a lead nut and screw coupling, the threaded element rotatable to move the first fastening member along the curvilinear guide;
    guide means configured to constrain the threaded element to the guide member to guide the threaded element along a predetermined movement direction.

2. The device according to claim 1, wherein the curvilinear guide defines an arc of a circle having a center which is movable to coincide with a center of rotation of the articulated bone elements.

3. The device according to claim 1, wherein the guide member comprises at least one slot defining the curvilinear guide.

4. The device according to claim 1, wherein the threaded element comprises:
    a first portion having left-handed threading which screwably engages one or the other of the first and second fastening members;
    a second portion having right-handed threading which screwably engages the other of the first and second fastening members.

5. The device according to claim 4, wherein the guide means comprise:
    a bushing integral with the threaded element at least along a direction of extension of the threaded element; and
    a socket for receiving the bushing, associated with the guide member and configured to constrain the bushing relative to the guide member and guide the bushing along the predetermined movement direction.

6. The device according to claim 1, wherein the second fastening member comprises a first portion and a second portion; the first portion being coupled to the curvilinear guide and the second portion comprising the second means for releasably fastening to the second bone element; the second fastening member comprising linear movement means to allow the second portion to move relative to the first portion during activation of the relative movement means by which the first fastening member is moved relative to the second fastening member along the curvilinear guide.

7. The device according to claim 6, wherein the linear movement means comprise a linear movement movable member slidably associated with a linear movement guide member to translate along the linear movement guide member; the linear movement guide member being coupled to the first portion and the linear movement movable member being coupled to the second portion.

8. The device according to claim 7, wherein the linear movement means comprise a locking means whereby the linear movement movable member is locked relative to the linear movement guide member, the locking means preventing the linear movement movable member and the linear movement guide member from moving relative to one another.

9. The device according to claim 6, wherein the guide means comprise:
   a bushing integral with the threaded element at least along a direction of extension of the threaded element; and
   a socket for receiving the bushing, associated with the guide member and configured to constrain the bushing relative to the guide member and guide the bushing along the predetermined movement direction.

10. The device according to claim 1, and further comprising a positioning rod attached to the guide member by which the guide member is positionable, the positioning rod being movable relative to the guide member in a plane parallel to a plane defined by the guide member and along a direction parallel to a radial direction relative to the curvilinear guide to allow one end of the positioning rod to be positioned at a line which is both normal to the plane defined by the guide member and which intersects a center of an arc defined by the curvilinear guide.

11. The device according to claim 1, wherein the guide means comprise:
   a bushing integral with the threaded element at least along a direction of extension of the threaded element; and
   a socket for receiving the bushing, associated with the guide member and configured to constrain the bushing relative to the guide member and guide the bushing along the predetermined movement direction.

12. A device for external fixation of a first bone element and a second bone element articulated to each other, comprising:
   a guide member equipped with a curvilinear guide;
   a first fastening member slidably associated with the curvilinear guide and equipped with first means for releasable fastening to the first bone element;
   a second fastening member associated with the curvilinear guide and equipped with second means for releasable fastening to the second bone element, the second fastening member being slidably associated with the curvilinear guide; and
   relative movement means by which the first fastening member is moved relative to the second fastening member along the curvilinear guide, wherein the relative movement means are configured to operate simultaneously on both the first fastening member and on the second fastening member in such a way as to move the first fastening member and the second fastening member along the curvilinear guide;
   wherein the second fastening member comprises a first portion and a second portion; the first portion being coupled to the curvilinear guide and the second portion comprising the second means for releasably fastening to the second bone element; the second fastening member comprising linear movement means to allow the second portion to move relative to the first portion during activation of the relative movement means by which the first fastening member is moved relative to the second fastening member along the curvilinear guide.

13. The device according to claim 12, wherein the linear movement means comprise a linear movement movable member slidably associated with a linear movement guide member to translate along the linear movement guide member; the linear movement guide member being coupled to the first portion and the linear movement movable member being coupled to the second portion.

14. The device according to claim 13, wherein the linear movement means comprise a locking means whereby the linear movement movable member is locked relative to the linear movement guide member, the locking means preventing the linear movement movable member and the linear movement guide member from moving relative to one another.

15. The device according to claim 14, wherein the relative movement means comprise an at least partly threaded element screwed at least to the first fastening member to define a lead nut and screw coupling, the threaded element rotatable to move the first fastening member along the curvilinear guide.

16. The device according to claim 12, wherein the relative movement means comprise an at least partly threaded element screwed at least to the first fastening member to define a lead nut and screw coupling, the threaded element rotatable to move the first fastening member along the curvilinear guide.

* * * * *